US009670452B2

(12) United States Patent
Dracker et al.

(10) Patent No.: US 9,670,452 B2
(45) Date of Patent: Jun. 6, 2017

(54) PROCUREMENT STAND FOR STEM CELL COLLECTION AND TRANSPORT

(71) Applicant: Americord Registry LLC, New York, NY (US)

(72) Inventors: Robert A. Dracker, Liverpool, NY (US); Martin P. Smithmyer, New York, NY (US)

(73) Assignee: AMERICORD REGISTRY LLC, New York, NY (US)

( * ) Notice: Subject to any disclaimer, the term of this patent is extended or adjusted under 35 U.S.C. 154(b) by 118 days.

(21) Appl. No.: 14/276,136

(22) Filed: May 13, 2014

(65) Prior Publication Data

US 2015/0329818 A1 Nov. 19, 2015

(51) Int. Cl.
| | |
|---|---|
| *C12M 1/00* | (2006.01) |
| *A47F 5/11* | (2006.01) |
| *A47B 47/06* | (2006.01) |
| *A47B 55/06* | (2006.01) |
| *A47B 43/02* | (2006.01) |

(52) U.S. Cl.
CPC ............ *C12M 45/00* (2013.01); *C12M 47/02* (2013.01); *A47B 43/02* (2013.01); *A47B 47/06* (2013.01); *A47B 55/06* (2013.01); *A47F 5/112* (2013.01); *A47F 5/114* (2013.01); *A47F 5/116* (2013.01)

(58) Field of Classification Search
CPC . C12M 47/02; A47F 5/11; A47F 5/112; A47F 5/114; A47F 5/116; A47B 43/02; A47B 47/06; A47B 55/06
See application file for complete search history.

(56) References Cited

U.S. PATENT DOCUMENTS

| | | | |
|---|---|---|---|
| 2003/0150771 A1* | 8/2003 | Mason et al. ........... | A47F 5/112 206/736 |
| 2011/0226717 A1* | 9/2011 | Mestres Armengol et al. ...................... | A47F 5/112 211/149 |

* cited by examiner

*Primary Examiner* — Gautam Prakash
(74) *Attorney, Agent, or Firm* — Bond Schoeneck & King, PLLC; Blaine Bettinger; George McGuire (57) ABSTRACT

A stand for the collection of stem cells from a placenta is disclosed. The stand includes a base with an upper surface adapted to hold a placenta during stem cell collection, a back support, and an upper platform with a surface suspended above the base and adapted to hold the placenta during collection of stem cells. The stand is preferably composed of cardboard or a similar material and is foldable between a folded configuration and an assembled configuration. The back support is hinged to the base and can move between a position parallel to the base in the folded configuration and a position perpendicular to the base in the assembled configuration.

13 Claims, 10 Drawing Sheets

PROCUREMENT STAND FOR STEM CELL COLLECTION AND TRANSPORT

BACKGROUND OF THE INVENTION

The present invention relates to procurement of cord blood and placental stem cells and, more specifically, to devices and systems, and methods for manipulating and holding a placenta during procurement of cord blood and placental stem cells.

Stem cells are master cells found in all multicellular organisms. These special cells are important to the human body, for example, because they are capable of differentiating into a multitude of different specialized cell types, and dividing to maintain a supply of stem cells. In humans there are two main types of stems cells: embryonic stem cells and adult stem cells. In a developing embryo stem cells differentiate into all types of cells, thereby creating specialized tissues, organs, and systems. In an adult human, stem cells are involved in the normal turnover of organs such as blood and skin.

Hematopoietic stem cells, for example, are used to treat blood and immune system diseases because they can differentiate into red blood cells, white blood cells, and platelets. However, some stem cell transplants have been performed for patients with genetic or metabolic diseases. Indeed, to date more than 80 different diseases have been treated using stem cell transplants. According to the National Cord Blood Program, there were over 15,000 through the end of 2009. The National Marrow Donor Program estimates that there will be 10,000 cord blood transplants per year by 2015, up from 2,000 per year in 2006.

In addition to known treatments involving stem cells, research continues into the promise of many potential future applications. Indeed, the ability of stem cells to differentiate into other types of cells holds significant promise for treating some of the world's most common diseases including heart disease, diabetes, stroke, hearing loss, blood disorders, Parkinson's disease, and Alzheimer's disease, just to name a few.

Umbilical cord blood—blood which remains in the placenta and umbilical cord after childbirth—is one of the most common sources of stem cells. Since cord blood is collected from the placenta, which is normally discarded, the collection process is safe for both the mother and the newborn. Cord blood is obtained by syringing out the placenta through the umbilical cord shortly after childbirth, after the cord has been detached from the newborn. The retrieved blood can then be frozen and stored indefinitely.

Although the amount of stem cells obtained from cord blood is generally enough to treat a child, there are generally not enough stem cells to treat an adult patient. The placenta is a better source of stem cells, since it can contain up to ten times more stem cells than cord blood. Still, even when blood is retrieved from both the umbilical cord and placenta using current collection methods, the amount of stem cells is often not suitable to treat an adult patient. As a result, there is a continued need for cord blood collection methods and devices that significantly increase the number of stem cells collected, facilitate the collection of stem cells, and allow for the collection of enough stem cells to treat at least one adult patient.

There is also a continued need for devices that manipulate and hold the placenta during stem cell collection. These devices must be both affordable and rugged in order to facilitate stem cell collection without error or added cost.

BRIEF SUMMARY OF THE INVENTION

It is therefore a principal object and advantage of the present invention to provide a method, device, and/or system for manipulating a placenta. It is another object and advantage to provide a device to facilitate the ingress and egress of stem cell procurement fluids into and out of a placenta. Other objects and advantages of the present invention will in part be obvious, and in part appear hereinafter.

The present disclosure is therefore directed to inventive apparatus and methods for manipulating, positioning, and/or holding a placenta during the collection of stem cells from the placenta. In view of the foregoing, various embodiments are directed to a compact collection stand that is composed of one or more pieces. The compact collection stand is manufactured to adopt at least two configurations—a compact folded configuration adapted for transport and storage of the device, and an expanded unfolded configuration adapted for use of the device. In some embodiments, the compact collection stand is also disposable. For example, the compact collection stand can be made of cardboard or a similar recyclable or disposable material, including but not limited to various varieties of plastic.

Generally, in one aspect, a stand for preparing and collecting a plurality of stem cells from a placenta is convertible between a folded configuration and an assembled configuration. The stand includes a base portion having an upper surface adapted to hold at least a portion of a placenta; an upper platform positionable in a horizontal orientation and having an upper surface substantially parallel to the upper surface of the base portion and adapted to hold at least a portion of a placenta; and a back support coupled to the upper platform and in hinged communication with the base portion such that the upper platform is suspended above the base when the stand is in the assembled configuration, the back support including a foldably positionable first arm and a foldably positionable second arm, where the first and second arms are substantially parallel with the upper surface of the base when the stand is in the folded configuration, and are substantially perpendicular to the upper surface of the base when the stand is in the assembled configuration.

In some embodiments, the upper platform includes a front flap in hinged communication with the upper surface of the upper platform and configured to fold substantially underneath the upper surface of the upper platform when the stand is in the assembled configuration.

In some embodiments, the front flap of the upper platform defines first and second slots, the first arm includes a first tab, and the second arm defines a second tab, where the first tab is configured to reversibly fit into the first slot and the second tab is configured to reversibly fit into the second slot when the stand is in the assembled configuration.

In some embodiments, the upper platform defines a first slot and the back support includes a first tab, the first tab configured to fit into the first slot when the stand is in the assembled configuration.

In some embodiments, the back support defines first and second slots, the first arm includes a first tab, and the second arm defines a second tab, where the first tab is configured to reversibly fit into the first slot and the second tab is configured to reversibly fit into the second slot when the stand is in the assembled configuration.

In some embodiments, the base defines a cavity.

In some embodiments, the upper platform includes a notch sized to firmly receive at least a portion of an umbilical cord.

In some embodiments, the stand is made of cardboard.

Generally, in one aspect, a stand for preparing and collecting a plurality of stem cells from a placenta is convertible between a folded configuration and an assembled configuration. The stand includes a base portion having an upper surface adapted to hold at least a portion of a placenta; an upper platform positionable in a horizontal orientation and having an upper surface substantially parallel to the upper surface of the base portion and adapted to hold at least a portion of a placenta, where the upper platform includes a front flap in hinged communication with the upper surface of the upper platform and configured to fold substantially underneath the upper surface of the upper platform when the stand is in the assembled configuration, and further where the front flap defines first and second flap slots; and a back support coupled to the upper platform and in hinged communication with the base portion such that the upper platform is suspended above the base when the stand is in the assembled configuration, the back support defining first and second support slots and including a foldably positionable first arm and a foldably positionable second arm, each of the first and second arms including a flap tab and a support tab, where the first and second arms are substantially parallel with the upper surface of the base when the stand is in the folded configuration, and are substantially perpendicular to the upper surface of the base when the stand is in the assembled configuration; where the flap tab of the first and second arms is configured to reversibly fit into the first and second flap slot, respectively, of the upper support front flap when the stand is in the assembled configuration, and further where the support tab of the first and second arms is configured to reversibly fit into the first and second support slot, respectively, when the stand is in the assembled configuration.

In some embodiments, the stand is made of cardboard.

In some embodiments, the upper platform defines a back support slot and the back support includes a back support tab, the back support tab configured to fit into the back support slot when the stand is in the assembled configuration.

In some embodiments, the base defines a cavity.

In some embodiments, the upper platform includes a notch sized to firmly receive at least a portion of an umbilical cord.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

It is desirable to obtain umbilical cord and placental blood in order to harvest the stem cells contained within them. These stem cells then have a variety of uses, both in basic science research and in treatment of disease. For example, stem cell transplants have been performed for patients with genetic or metabolic diseases, and to date more than 80 different diseases have been treated using stem cell transplants. However, the amount of stem cells obtained from both the umbilical cord and placenta using previous collection methods is generally not enough to treat an adult patient.

Accordingly, Applicants have appreciated that it would be beneficial to provide methods and devices that manipulate, position, and hold the umbilical cord and placenta to maximize the inflow and outflow of blood and other fluids during stem cell collection.

In view of the foregoing, various embodiments are directed to inventive apparatus and methods for manipulating, positioning, and/or holding a placenta using compact collection stand that is composed of one or more pieces. The compact collection stand is manufactured to adopt at least two configurations—a compact folded configuration adapted for transport and storage of the device, and an expanded unfolded configuration adapted for use of the device. In some embodiments, the compact collection stand is also disposable. For example, the compact collection stand can be made of cardboard or a similar recyclable or disposable material, including but not limited to various varieties of plastic.

Figure 1:
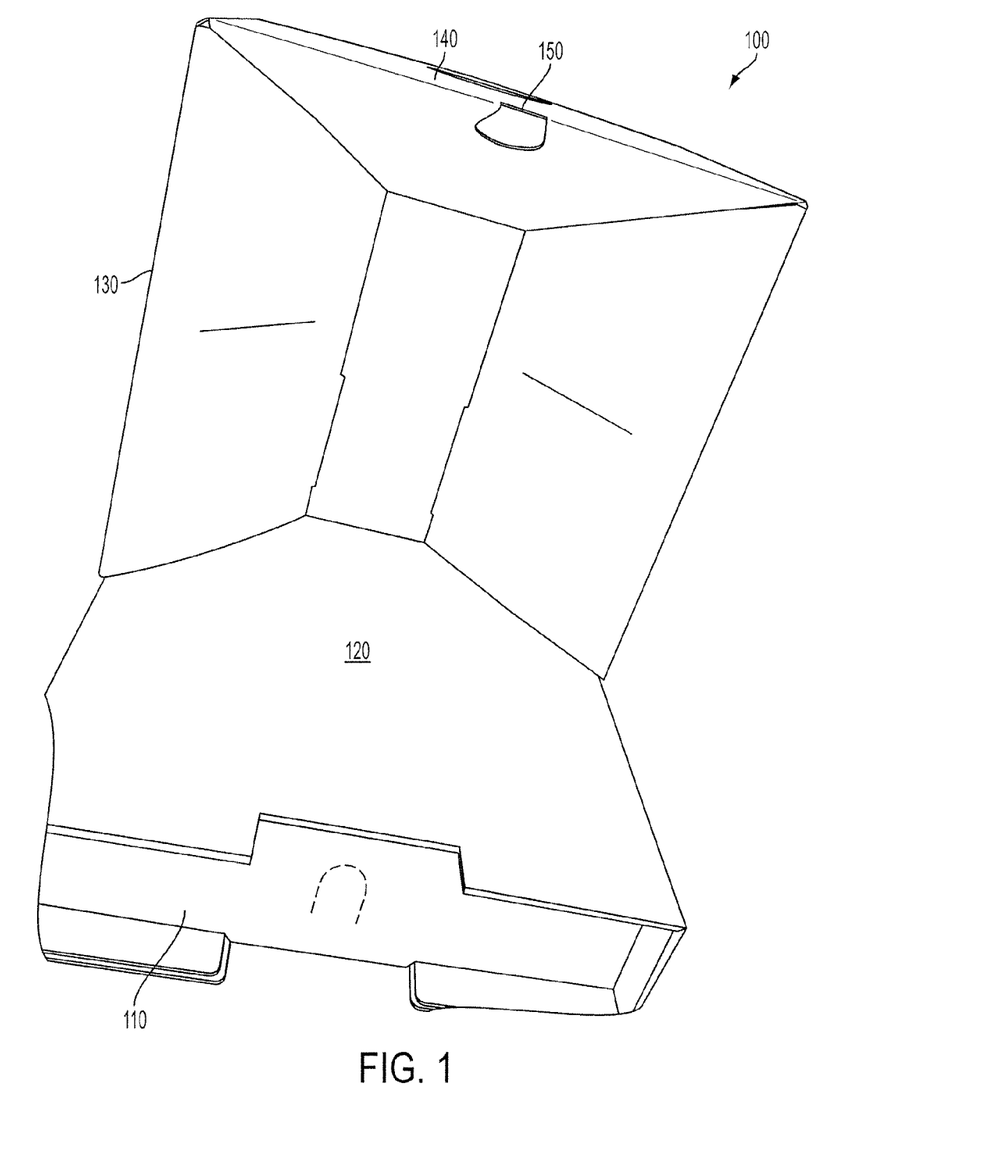
FIG. 1 is a front view of an assembled procurement stand in accordance with an embodiment of the invention.

Referring to FIG. 1 is a front view of a stem cell procurement stand 100 in accordance with one embodiment, which facilitates the ingress and egress of stem cell procurement fluids into and out of the placenta after delivery. The device preferably is made of a material such as cardboard or plastic, although a variety of suitable materials are possible. For example, stem cell procurement stand 100 may be composed of a material that allows the device to at least partially fold at one or more locations such that the device is collapsible and/or disposable. According to one embodiment, therefore, stem cell procurement stand 100 is foldable and is thus structured, adapted, and/or configured to adopt two different configurations: a first, collapsed configuration suitable for transporting or storing the device, and a second, expanded configuration that enables the device to be utilized for stem cell procurement.

As shown in FIG. 1, stem cell procurement stand 100 includes a base 110 which is preferably dimensioned such that it can comfortably hold a placenta in the region denoted lower placenta receiving area 120. In a preferred embodiment and method, the placenta is placed 'umbilical cord side up' in lower placenta receiving area 120 in order to facilitate the influx of fluids into the cord and placenta via gravity.

Extending vertically upward from base 110 is backing 130 of the device. Backing 130 has an upper shelf 140, which is dimensioned to hold the placenta. In a preferred embodiment, the placenta is placed 'umbilical cord side down' on upper shelf 140 to allow fluids to exit the cord and placenta via gravity. To maximize the effect of gravity, the umbilical cord is preferably positioned into a notch 150 in or near upper shelf 140 such that fluids in the placenta can flow toward and into the umbilical cord and then into a collection device such as a bag or other container. In one embodiment, notch 150 can also hold or receive a portion of a bag containing stem cell procurement fluid which is loaded into the placenta during loading, and can also hold or receive a bag into which the stem cell procurement fluid is unloaded from the placenta during unloading.

A wide range of dimensions for the device are possible, although according to one embodiment the dimensions are at least partially derived from the average size of the placenta from the particular mammal it will be used for. For example, if the stand is used for humans, the recesses will be sized to hold at least the average human placenta, and the remainder of the stand will be sized based on the size of the recesses.

Stem cell procurement stand 100 is preferably used to facilitate the loading and unloading of stem cell procurement fluid. At a first step of procurement using the device according to one embodiment, the placenta is placed in lower placenta receiving area 120 and a bag containing the procurement fluid is clipped onto the device or placed on top of the device on shelf 140. A needle or tube from the bag is inserted into the umbilical cord and/or placenta, and the fluid from the bag is allowed to load into the placenta via the umbilical cord. The placenta may be manipulated to encourage loading.

At a second step of procurement using stem cell procurement stand 100 according to one embodiment, the placenta is placed upper shelf 140 of the device with the umbilical cord in the provided notch 150, and a collection bag is clipped onto the device. A needle or tube from the bag is inserted into the umbilical cord and/or placenta, and the fluid from the placenta is allowed to load into the bag via the umbilical cord. The placenta may be manipulated to encourage unloading.

Figure 7:
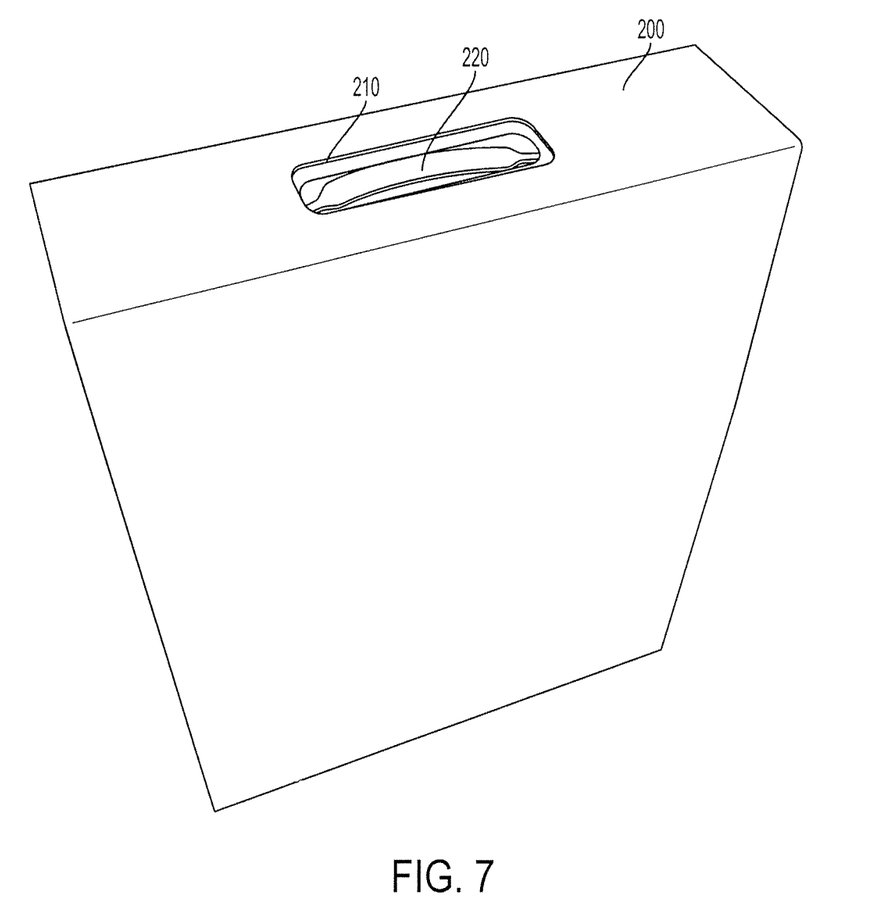
FIG. 7 is a prospective view of a procurement stand in its carrying case in accordance with an embodiment of the invention.
Figure 8:
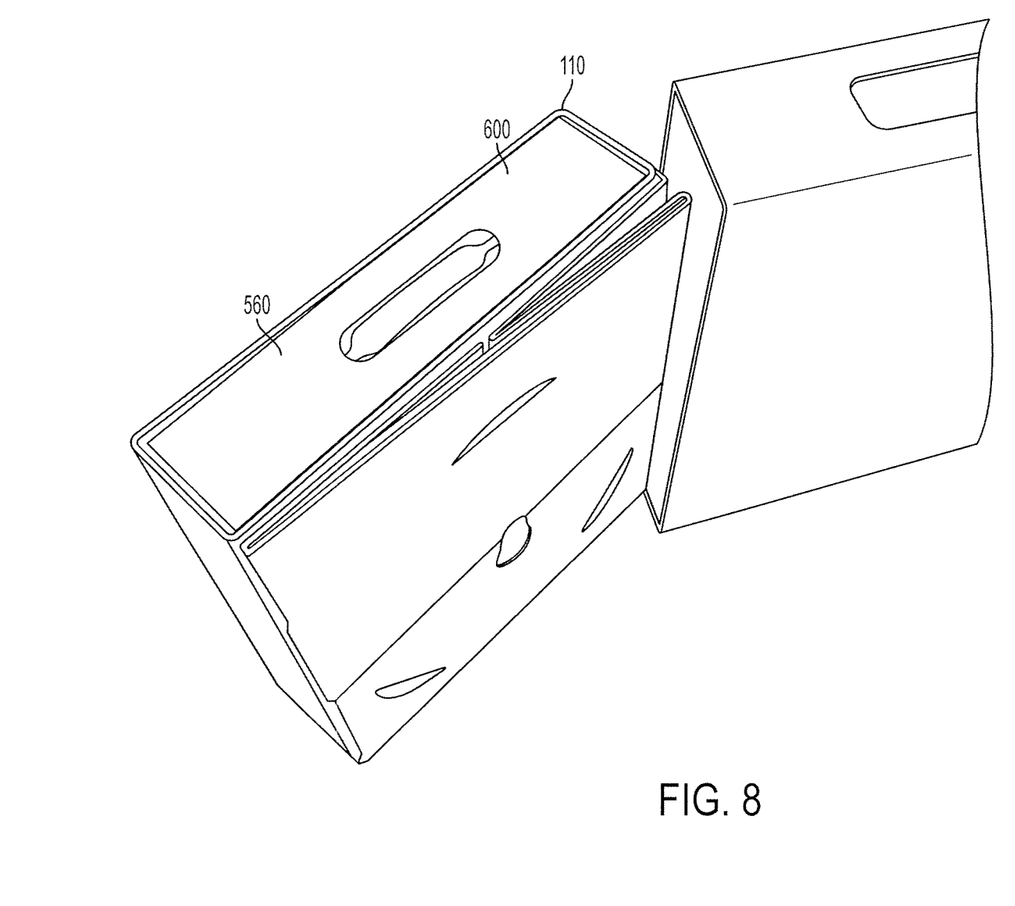
FIG. 8 is a prospective view of a collapsed procurement stand removed from its carrying case in accordance with an embodiment of the invention.

In accordance with an embodiment, stem cell procurement stand 100 is reversibly collapsible and foldable between a first configuration and a second configuration. In a first configuration, shown in FIGS. 7 and 8, stem cell procurement stand 100 comprises two or more pieces folded and collapsed into a carrying case 200. Stem cell procurement stand 100 can be folded, shipped, and/or stored with or without carrying case 200. Carrying case 200 preferably comprises a material such as cardboard or plastic, although a variety of suitable materials are possible, and contains a notch 210 configured to allow the exposure and manipulation of a handle 220. According to a preferred embodiment, carrying case 200 has open sides or has one or more side panels that can be moved, opened, or removed to allow folded stem cell procurement stand 100 to be placed into or withdrawn from the interior of the carrying case. As shown in FIG. 8, for example, stem cell procurement stand 100 can be withdrawn from carrying case 200 in its folded configuration.

Figure 2:
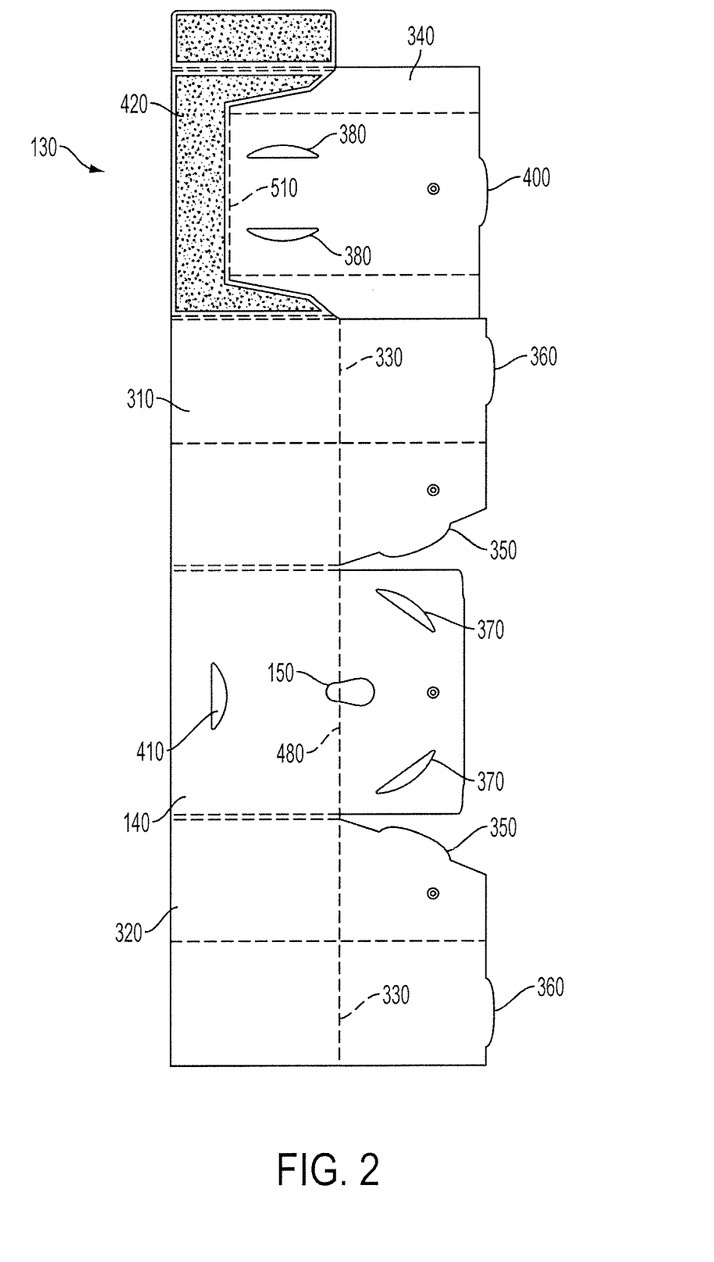
FIG. 2 is a schematic of an upper portion of a procurement stand in accordance with an embodiment of the invention.
Figure 9:
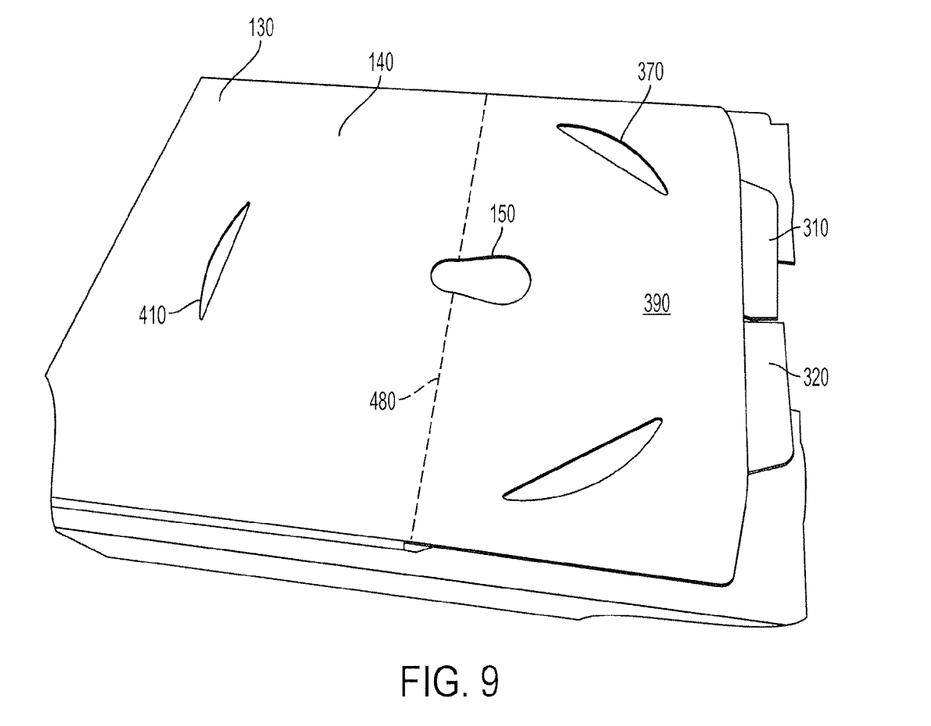
FIG. 9 is a top view of a collapsed procurement stand in accordance with an embodiment of the invention.
Figure 10:
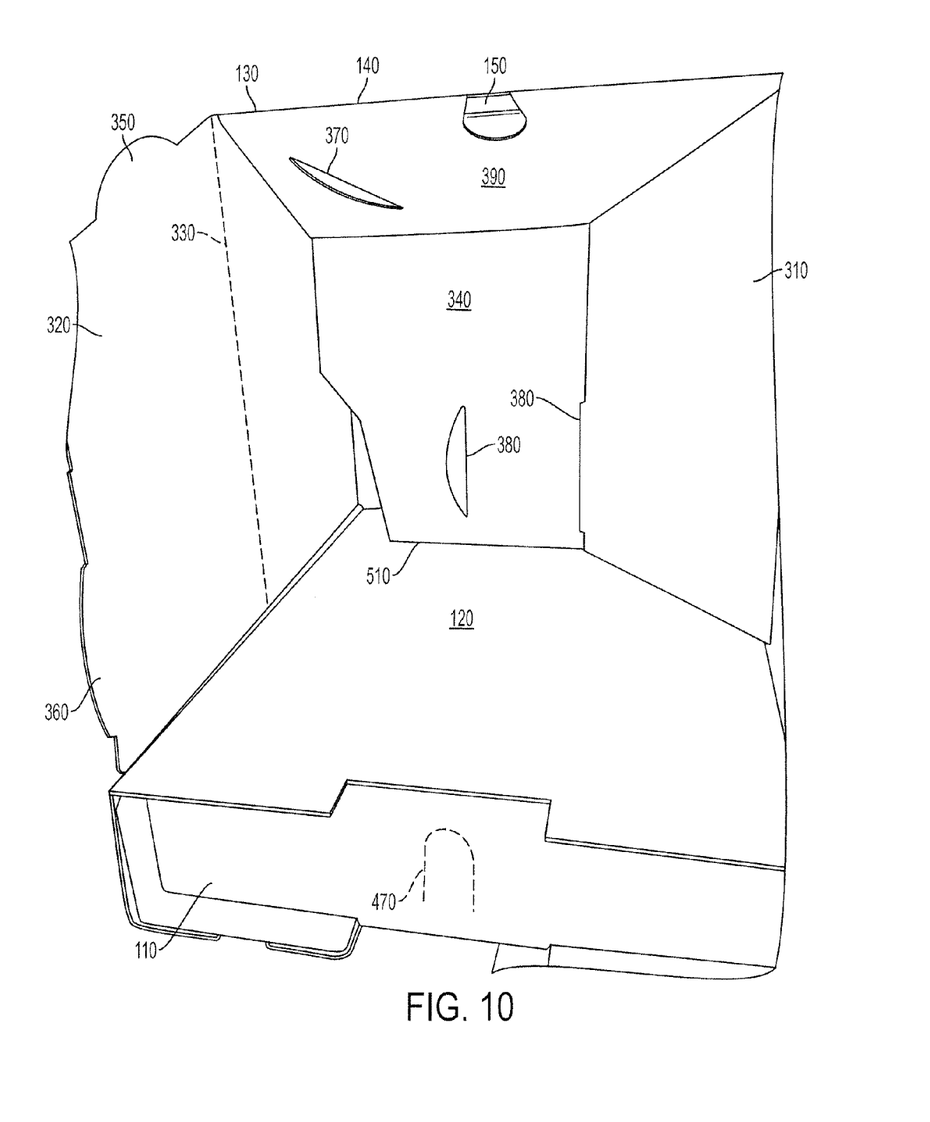
FIG. 10 is a front view of a partially assembled procurement stand in accordance with an embodiment of the invention.

In its first, folded configuration, the backing 130 of stem cell procurement stand 100 is folded nearly flat, as shown in FIG. 9. To assemble the backing 130 for use, the upper portion 140 of folded backing 130 in FIG. 7 is pulled vertically upward, and arms 310 and 320 of the backing are extended. Each arm has a pre-folded or perforated fold 330 (see FIG. 2) that allows a front half of the arm to fold back on itself toward the rear support wall 340 of backing 130 (shown in FIG. 10). In these and other figures, dotted lines indicate where a fold can occur in the first configuration, the second configuration, or both. A dotted line may be pre-folded or perforated, or may otherwise be configured to allow or facilitate folding. Each arm has an upper tab 350 and a lower tab 360. Upper tab 350 of each arm fits into a respective one of upper slots 370 of upper portion 140 of backing 130, and lower tab 360 of each arm fits into a respective one of lower slots 380 of rear support wall 340. Upper portion 140 of backing 130 has a front flap 390 that folds along a pre-folded or perforated fold 480 (see FIG. 9) under upper portion 140, such that the fold faces the interior section of the backing, as shown in FIG. 10. This folding places upper slots 370 into opposition with upper tabs 350 to allow the upper portion of the stand to be assembled. The forces exerted between base 110 and upper portion 140 on arms 310 and 320 keeps the device firmly folded and structurally sound.

In the first, folded configuration of backing 130, rear support wall 340 is flat underneath upper portion 140 and arms 310 and 320 (see FIG. 9, for example). In the second, expanded configuration of backing 130, rear support wall 340 is pulled vertically upward and upper tab 400 of the rear wall is placed into slot 410 of upper portion 140 (shown in FIG. 9). In one embodiment, the lower portion 420 of rear support wall 340 is attached to base 110. In one embodiment, backing 130 is manufactured as a portion of base 110, or is attached to base 110 during or after manufacturing. Alternatively, backing 130 can rest on top of base 110, or can connect to 110 by VELCRO® fasteners, glue, tape, or other connecting mechanism. For example, in one embodiment, lower portion 420 of rear support wall 340 (shown in FIG. 2 in shading) is glued or otherwise connected to shaded region 430 of base 110. This allows the rear support wall to stay connected to base 110 at all times, but can hinge at fold 510 so that rear support wall can adopt both the flat configuration (FIG. 9) and the upright configuration (FIG. 10).

Figure 3:
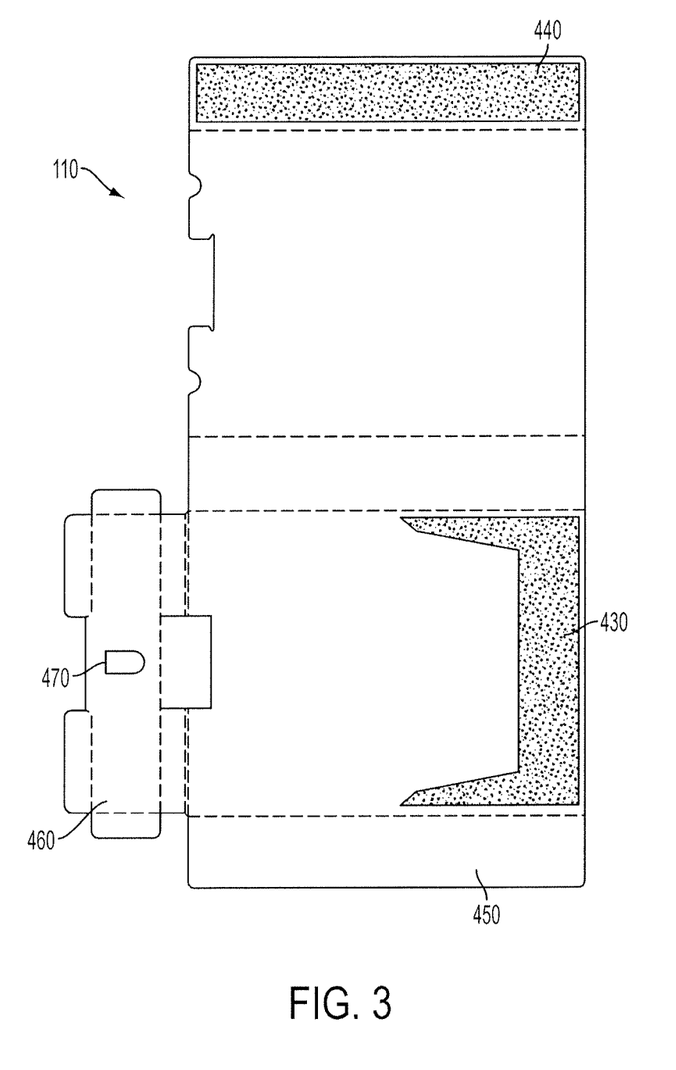
FIG. 3 is a schematic of a base of a procurement stand in accordance with an embodiment of the invention.
Figure 4:
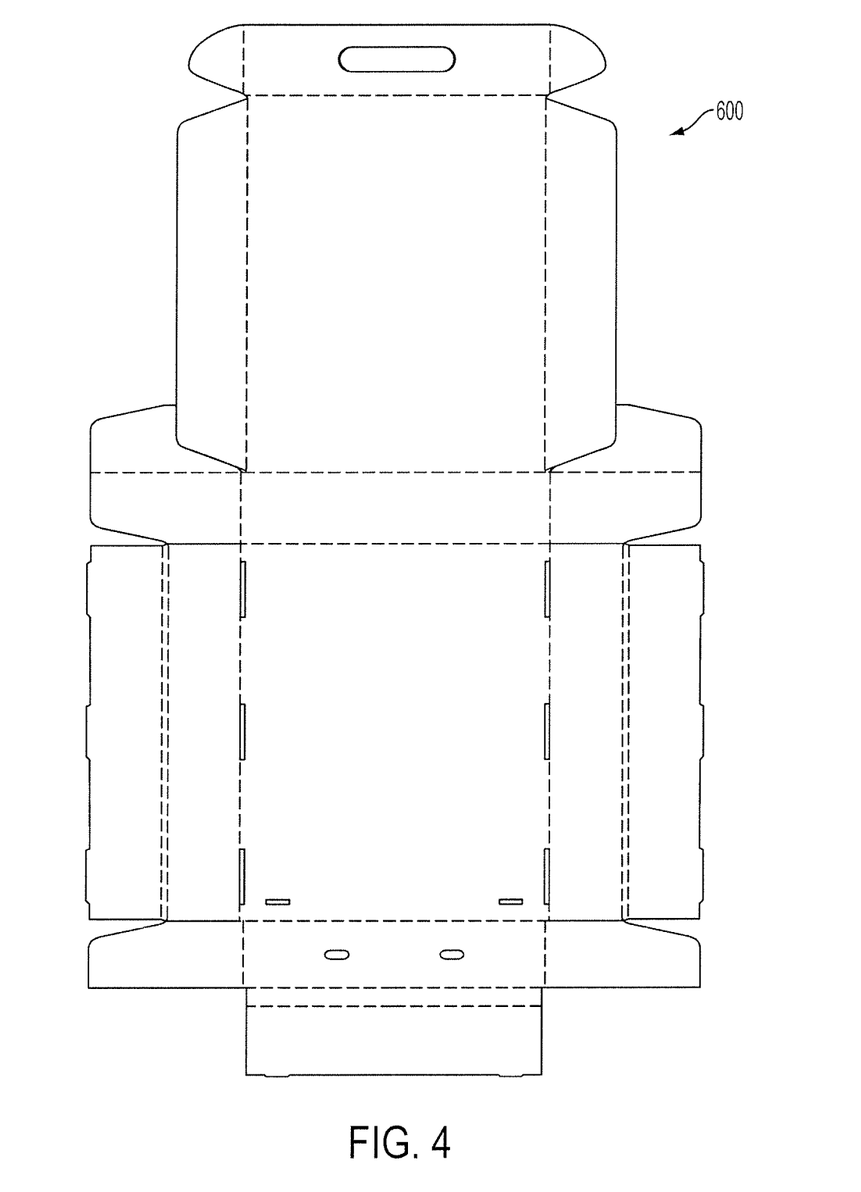
FIG. 4 is a schematic of a collection kit in accordance with an embodiment of the invention.
Figure 5:
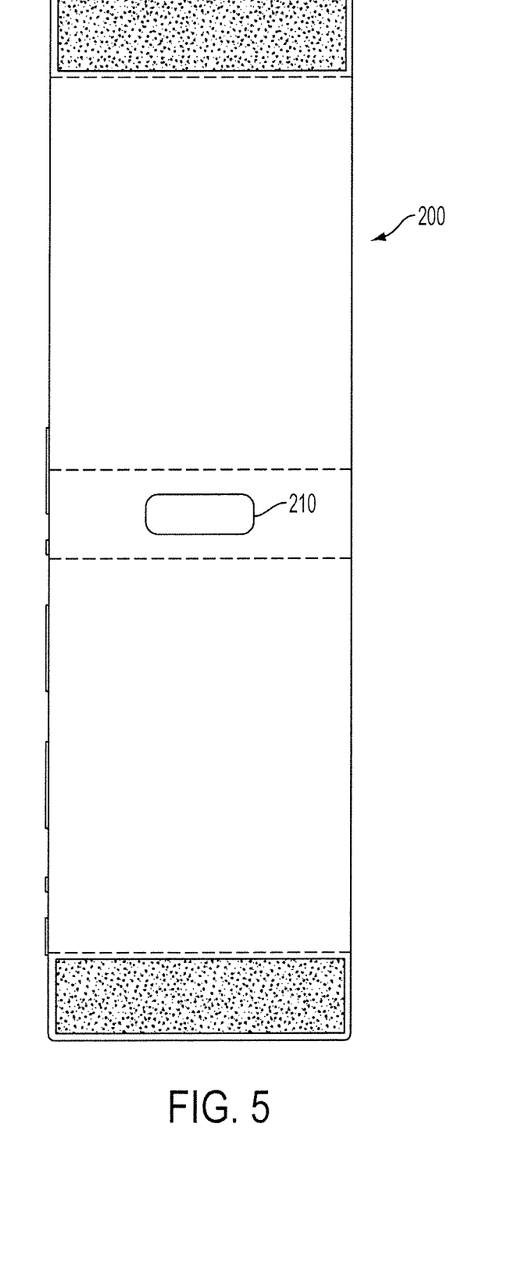
FIG. 5 is a schematic of a kit sleeve in accordance with an embodiment of the invention.

Similarly, in one embodiment, shaded portion 440 of base 110 (shown in FIG. 3) can be glued or otherwise connected to flap 450 in order to create a folded, rectangular base 110 as depicted in FIGS. 1 and 10, for example. The front flap 460 of base 110 preferably faces forward, and notch 470 of front flap 460 faces forward. Notch 470 is can be used for a variety of functions, including holding a collection bag or container and/or a solution bag or container. The folded rectangular base 110 as depicted in FIGS. 1 and 10 also forms a pocket or cavity 560, as the base 110 can lack a back (see, for example, FIG. 3, in which base 110 lacks a back flap) or include a flap or other movable covering that allows access to an interior pocket of base 110. FIG. 8, for example, shows a collection kit 600 (schematic shown in FIG. 4) that has been placed inside the pocket or cavity 560 formed in the back of base 110. The edges of the pocket are shown around the collection kit 600.

Accordingly, to assemble a stem cell collection stand from a first, folded configuration to a second, assembled configuration, the following steps are performed. First, a folded stand 100 is provided, as shown in FIG. 7. Next, the folded components are removed from the case 200, as shown in FIGS. 8 and 9. Next, the upper portion 130 is pulled upward, and rear support 340 (which is connected at its base to the base 110) is pulled upward, hinging at fold 510 so that backing 130 is vertical between the base 110 and upper portion 130, as shown in FIG. 10, with tab 400 of rear support 340 fitting into slot 410 of upper portion 130. Arms 310 and 320 are pulled outward from the flat configuration in FIG. 9 to the extended configuration (see arm 320 in FIG. 10). Front flap 390 of upper portion 130 is folded underneath so that the flap faces the interior of the vertical portion of the device, as shown in FIG. 10. Each of arms 310 and 320 are folded backward toward backing 130, such that tabs 350 of each arm fit into slots 370 of the folded front flap 390 of upper portion 130, and tabs 360 of each arm fit into slots 380 of rear support wall 340, as shown in FIG. 10. Device 100 is now in the second, assembled configuration shown in FIG. 1.

Figure 6:
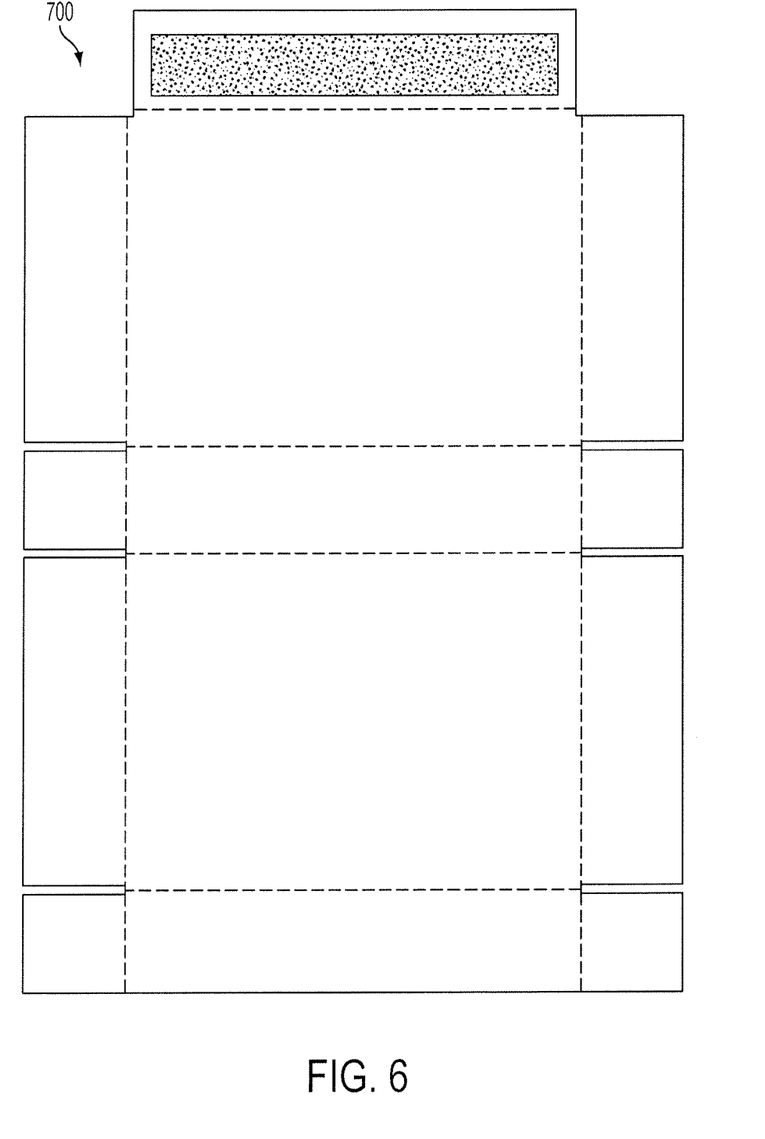
FIG. 6 is a schematic of a shipping case in accordance with an embodiment of the invention.

In addition to facilitating the ingress and egress of stem cell procurement fluids into and out of a placenta, maximizing efficient stem cell collection also often requires the secure transport of the placenta from one location to another. According to one embodiment, the kit can also include a shipping container 700, as shown in FIG. 6. The shipping container can be utilized to ship one or more components of the device and/or collection quantities (stem cells, placenta, cord blood, etc.) to a facility for storage or processing.

Although the present invention has been described in connection with a preferred embodiment, it should be understood that modifications, alterations, and additions can be made to the invention without departing from the scope of the invention as defined by the claims.

What is claimed is:

1. A stand for preparing and collecting umbilical cord blood and a plurality of stem cells from a placenta, the stand configured to be convertible between a folded configuration and an assembled configuration, the stand comprising:
    a base portion comprising an upper surface sized to hold a human placenta;
    an upper platform positionable in a horizontal orientation and having an upper surface substantially parallel to the upper surface of the base portion and sized to hold a human placenta; and
    a back support coupled to the upper platform and in hinged communication with the base portion such that the upper platform is suspended above the base when the stand is in the assembled configuration, the back support comprising a foldably positionable first arm and a foldably positionable second arm, wherein the first and second arms are substantially parallel with said upper surface of said base when the stand is in the folded configuration, and are substantially perpendicular to said upper surface of said base when the stand is in the assembled configuration, and further wherein the first and second arms are configured to be positioned on the upper surface of said base when the stand is in the assembled configuration.

2. The stand of claim 1, wherein said upper platform comprises a front flap in hinged communication with said upper surface of said upper platform and configured to fold substantially underneath said upper surface of said upper platform when said stand is in said assembled configuration.

3. The stand of claim 2, wherein said front flap of said upper platform defines first and second slots, the first arm comprises a first tab, and the second arm defines a second tab, wherein the first tab is configured to reversibly fit into the first slot and the second tab is configured to reversibly fit into the second slot when said stand is in said assembled configuration.

4. The stand of claim 1, wherein said upper platform defines a first slot and said back support comprises a first tab, the first tab configured to fit into the first slot when said stand is in said assembled configuration.

5. The stand of claim 1, wherein said back support defines first and second slots, the first arm comprises a first tab, and the second arm defines a second tab, wherein the first tab is configured to reversibly fit into the first slot and the second tab is configured to reversibly fit into the second slot when said stand is in said assembled configuration.

6. The stand of claim 1, wherein said base defines a cavity.

7. The stand of claim 1, wherein said upper platform comprises a notch sized to receive at least a portion of an umbilical cord.

8. The stand of claim 1, wherein said stand comprises cardboard.

9. A stand for preparing and collecting a plurality of stem cells from a placenta, the stand configured to be convertible between a folded configuration and an assembled configuration, the stand comprising:
    a base portion comprising an upper surface sized to hold a human placenta;
    an upper platform positionable in a horizontal orientation and having an upper surface substantially parallel to the upper surface of the base portion and sized to hold a human placenta, wherein the upper platform comprises a front flap in hinged communication with the upper surface of the upper platform and configured to fold substantially underneath the upper surface of the upper platform when the stand is in the assembled configuration, and further wherein the front flap defines first and second flap slots; and
    a back support coupled to the upper platform and in hinged communication with the base portion such that the upper platform is suspended above the base when the stand is in the assembled configuration, the back support defining first and second support slots and comprising a foldably positionable first arm and a foldably positionable second arm, each of said first and second arms comprising a flap tab and a support tab, wherein the first and second arms are substantially parallel with said upper surface of said base when the stand is in the folded configuration, and are substantially perpendicular to said upper surface of said base when the stand is in the assembled configuration, and further wherein the first and second arms are configured to be positioned on the upper surface of said base when the stand is in the assembled configuration;
    wherein the flap tab of the first and second arms is configured to reversibly fit into the first and second flap slot, respectively, of the upper support front flap when said stand is in said assembled configuration, and further wherein the support tab of the first and second arms is configured to reversibly fit into the first and second support slot, respectively, when said stand is in said assembled configuration.

10. The stand of claim 9, wherein said stand comprises cardboard.

11. The stand of claim 9, wherein the upper platform defines a back support slot and said back support comprises a back support tab, the back support tab configured to fit into the back support slot when said stand is in said assembled configuration.

12. The stand of claim 9, wherein said base defines a cavity.

13. The stand of claim 9, wherein said upper platform comprises a notch sized to receive at least a portion of an umbilical cord.

* * * * *